US006916820B1

(12) United States Patent
Kelley et al.

(10) Patent No.: US 6,916,820 B1
(45) Date of Patent: Jul. 12, 2005

(54) NEUROTROPHIC SUBSTITUTED PYRIMIDINES

(75) Inventors: James L. Kelley, Raleigh, NC (US); Thomas A. Krenitsky, Chapel Hill, NC (US); Lilia M. Beauchamp, Raleigh, NC (US)

(73) Assignee: Krenitsky Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/958,511

(22) PCT Filed: Apr. 6, 2000

(86) PCT No.: PCT/US00/09108

§ 371 (c)(1),
(2), (4) Date: Feb. 6, 2002

(87) PCT Pub. No.: WO00/61562

PCT Pub. Date: Oct. 19, 2000

Related U.S. Application Data

(63) Continuation-in-part of application No. 09/288,495, filed on Apr. 8, 1999, now Pat. No. 6,583,148.

(51) Int. Cl.$^7$ ..................... A61K 31/505; C07D 239/48
(52) U.S. Cl. ..................... 514/269; 514/272; 514/275; 544/298; 544/319; 544/323; 544/324; 544/330; 544/331; 544/332
(58) Field of Search ................................ 514/269, 272, 514/275; 544/319, 298, 330, 331, 332, 323, 324

(56) References Cited

U.S. PATENT DOCUMENTS

| | | | |
|---|---|---|---|
| 2,691,655 | A | 10/1954 | Hitchings et al. |
| 3,154,551 | A | 10/1964 | Hitchings et al. |
| 3,862,190 | A | 1/1975 | Lipinski et al. |
| 3,947,441 | A | 3/1976 | Schweizer et al. |
| 5,075,305 | A | 12/1991 | Hobbs et al. |
| 5,525,604 | A | 6/1996 | Lee et al. |
| 6,440,965 | B1 | 8/2002 | Kelley et al. ............. 514/232.2 |

FOREIGN PATENT DOCUMENTS

| | | |
|---|---|---|
| DE | 23 44 611 A | 3/1974 |
| DE | 25 33 710 A1 | 2/1976 |
| DE | 2 829 820 | 2/1979 |
| DE | 42 39 440 A1 | 6/1993 |
| EP | 0 372 934 A2 | 6/1990 |
| EP | 0 459 819 A2 | 12/1991 |
| EP | 0 465 323 A1 | 1/1992 |
| EP | 0 640 599 A1 | 3/1995 |
| EP | 0826 674 A1 | 3/1998 |
| FR | 2 358 148 | 2/1979 |
| JP | 08 283246 A | 10/1996 |
| WO | WO 92/18498 A1 | 10/1992 |
| WO | WO 93 08169 A1 | 4/1993 |
| WO | WO 94 14780 A1 | 7/1994 |
| WO | WO 96 31488 A1 | 10/1996 |
| WO | WO 99 19305 A2 | 4/1999 |

OTHER PUBLICATIONS

Aroyan, et al., "Pyrimidine derivatives. X. Synthesis of amino and hydrazino derivatives of 2–(methylthio)– 5–(p–alkoxybenzyl)–6–methyl pyrimidines, and a study of their antineoplastic activity", Chemical Abstracts, 1969, p. 347, vol. 71, No. 21.

Aroyan, et al., "Pyrimidine derivatives. XLIV. Synthesis and some reactions of 2–phenyl–4–hydroxy–5–(p–alkoxybenzyl)–6–methylpyrimidines", Chemical Abstracts, 1976, p. 515, vol. 84, No. 9.

Aroyan, et al., "Pyrimidine derivatives. XXXV. Synthesis of 2, 4–bis(arylamino)– and 2, 4–bis(aryloxy)—5– (p–alkoxybenzyl) –6–methylpyrimidines", Chemical Abstracts, 1975, p. 601, vol. 82, No. 23.

Aroyan, et al., "Synthesis and some reactions of 4–hydroxy–5–(p–alkoxybenzyl)–6–methyl–2–mercapto– (and 2–amino–)pyrimidines" Chemical Abstracts, 1968, p. 1241, vol. 68, No. 3.

Awaya, et al. *Neurotropic Pyrimidine Heterocycle Compounds. I. The Newly Synthesized Pyrimidine Compounds Promote Neurite Outgrowth of GOTO and Neuro 2a Neuroblastoma Cell Lines, and Potentiate Nerve Growth Factor (NGF)–Induced Neurite Sprouting of PC 12 Cells*, Biol. Pharm. Bull., 1993, pp. 248–253, Pharmaceutical Society of Japan, vol. 16(3).

Chemical Abstracts, 1997, p. 620, col. 2, vol. 126, No. 7, abstract No. 89387x.

Curd, et al. "74. Synthetic antimalarials. Part VII. 2–Arylamino–4–dialkylaminoalkylaminopyrimidines. Variation of substituents in the 5– and the 6–position" J. Chem. Soc., 1946, pp. 378–384.

E.A. Coats et al., "Correlation Analysis of Pyrimidine Folic Acid Antagonists as Antibacterial Agents .I.", Euro. J. Med. Chem.—Chemica Therapeutica, May 1979, pp. 261–270, vol. 14, No. 3, Editions Scientifique Elsevier, Paris.

Falco, et al. "5–Arylthiopyrimidines.1.2, 4–Diamino Derivatives", J. Org. Chem.., 1961, pp. 1143–1146, vol. 26.

Goldberg, A., "No. 218. Préparation de quelques 5–benzyl pyrimidines" Bulletin De La Societe Chimique France, 1951, pp. 895–899.

Hull, et al. "70. Synthetic antimalarials. Part III. Some derivatives of mono– and di–alkylpyrimidines", J. Chem. Soc., 1946, pp. 357–362.

Hull, et al. "9. Synthetic animalarials. Part XI. The effect of variation of substituents in derivatives of mono– and di–alkylpyrimidines" J. Chem. Soc., 1947, pp. 41–52.

(Continued)

Primary Examiner—Richard L. Raymond
(74) Attorney, Agent, or Firm—Alston & Bird LLP

(57) ABSTRACT

The present invention relates to a series of substituted pyrimidines, to pharmaceutical compositions which contain them, to methods for their preparation and to their use in therapy, particularly in the treatment of neurodegenerative or other neurological disorders of the central and peripheral nervous systems.

28 Claims, No Drawings

OTHER PUBLICATIONS

Kramer, et al., "Pyrimidine derivatives. XVI. 4-(p-Alkoxyphenyl)-2, 6-dimethyl-4-pyrimidinylaminophosphonic diaziridides", *Chemical Abstracts,* 1970, p. 326, vol. 73, No. 7.

Lehmann, et al., *Neurite Outgrowth of Neurons of Rat Dorsal Root Ganglia Induced By New Neurotrophic Substances With Guanidine Group,* Neuroscience Letters, 1993, pp. 57–60, Elsevier Scientific Publishers Ireland, Ltd. vol. 152.

Ordukhanyan, et al., "Study of the relation between structure and biological activity. II. Antineoplastic activity of pyrimidine derivatives", *Chemical Abstracts,* 1980, p. 25, vol. 92, No. 3.

Roth, et al. "5–Arylthiopyrimidines. II. 2– and 4–Alkylamino and 4–Amino Derivatives", *J. Org. Chem..,* 1961, pp. 2770–2778, vol. 26.

Roth, et al. "5–Benzyl–2,4–diaminopyrimidines as antibacterial agents. I. Synthesis and antibacterial activity in vitro" *J. Med. Pharm. Chem,.,* 1962, pp. 1103–1123, vol. 5.

Samano, et al., "An Improved Synthesis of 2–Amino–5–[(4–chlorophenyl)thio]–4–morpholinopyrimidine (BW 394U)—A Potential Antisenility Agent", *J. Heterocyclic Chem.,* Jan.–Feb. 2000, pp. 183–185, vol. 37.

Vaillancourt, et al., "Synthesis and Self–Association of 4–Pyrimidinones", *J. Org. Chem.,* 1998, pp. 9746–9752, vol. 63, No. 26.

Chemical Abstracts, 1966, Abstract No. 6328–42–3.

NEUROTROPHIC SUBSTITUTED PYRIMIDINES

CROSS-REFERENCE TO RELATED APPLICATIONS

This application is a 35 U.S.C. 371 national phase application of International Application No. PCT/US00/09108, filed Apr. 6, 2000, which is a continuation-in-part of U.S. patent application Ser. No. 09/288,495, filed Apr. 8, 1999, now U.S. Pat. No. 6,583,148, both of which are incorporated herein in their entirety.

BACKGROUND OF THE INVENTION

The present invention relates to novel derivatives of a series of substituted pyrimidines, to pharmaceutical compositions which contain them, to methods for their preparation and to their use in therapy, particularly in the treatment of neurodegerative or other neurological disorders of the central and peripheral systems including nerve injuries.

Dementing disorders such as age-related cognitive disorders, e.g., senility or Alzheimer's disease are medical conditions for which there are currently only limited therapies. Although studies suggest that multiple neurotransmitter systems are involved in senile dementia, a loss of cholinergic neurons and a severe depletion of choline acetyltransferase appear to show the earliest and strongest correlations with functional cognitive impairment [see P. T. Francis et al., Neurochemical Studies of Early-onset Alzheimer's Disease. N. Engl. J. Med., 313, 7 (1985); R. T. Bartus et al., The Cholinergic Hypothesis: A Historical Overview, Current Perspective, and Future Directions. Ann. N. Y. Acad. Sci., 444, 332 (1985); F. Hefti and L. S. Schneider, Nerve Growth Factor and Alzheimer's Disease, Clin. Neuropharmacol., 14, S62 (1991)]. Several groups have attempted to stimulate cholinergic activity by blocking the breakdown of acetylcholine with acetylcholine esterase inhibitors or by introducing muscarinic or nicotinic agonists [see R. T. Bartus et al., The Cholinergic Hypothesis of Geriatric Memory Dysfunction. Science, 217, 408 (1982); J. Varghese et al., Chapter 21. Alzheimer's Disease: Current Therapeutic Approaches. Annu. Rep. Med. Chem., 28, 197 (1993)]. The approved drugs Cognex and Aricept are acetylcholine esterase inhibitors.

Nerve growth factor (NGF) is the best characterized neurotrophic factor that is capable of inducing cell differentiation of neural cells and promoting neurite sprouting. The neurotrophic protein NGF primarily affects cholinergic neurons in the central nervous system and may be necessary for their survival [see F. Hefti and P. A. Lapchak, Pharmacology of Nerve Growth Factor in the Brain. Adv. Pharmacol., 24, 239 (1993)]. NGF is not systemically bioavailable, but if it is injected or infused directly into brain, it prevents neuronal cell loss and restores cognitive function in aged or lesioned rats or monkeys [see W. Fischer et al., NGF Improves Spatial Memory in Aged Rodents as a Function of Age. J. Neurosci, 11, 1889 (1991)]. NGF effects ultimately result in the stimulation of choline acetyltransferase, the enzyme for biosynthesis of acetylcholine and the promotion of neurite growth. Consequently, small molecules that produce neurotrophic or "nerve growth factor-like" (NGF-like) properties in mammalian cell cultures have potential for use in the treatment of dementing disorders such as age-related senility or Alzheimer's disease and other neurodegenerative conditions such as peripheral neuropathies, Parkinson's, stroke damage, transient ischemic attacks, trauma-head injuries or other nerve injuries.

There are several reports of small molecules that exhibit various aspects of NGF-like activity. Isaxonine [2-(isopropylamino)pyrimidine] was developed as a neurotrophic pharmaceutical but the clinical application was withdrawn, possibly due to toxicological effects [see S. Lehmann et al., Neurite Outgrowth of Neurons of Rat Dorsal Root Ganglia Induced by New Neurotrophic Substances with Guanidine Group. Neurosci. Lett., 152, 57 (1993)]. Several 2-(piperazino)pyrimidine derivatives were reported to possess NGF-like activity and are being studies further for use in treating CNS degenerative diseases [see A. Awaya et al., Neurotrophic Pyrimidine Heterocyclic Compound. Biol. Pharm. Bull., 16, 248 (1993)]. AIT-082 (4[[3-(1,6-dihydro-6-oxo-9-purin-9-yl)-1-oxopropyl]amino]benzoic acid) is reported to enhance NGF action in cultured PC-12 cells and to restore age-induced working memory deficits in mice [see P. J. Middlemiss et al., AIT-082, A Unique Purine Derivative, Enhances Nerve Growth Factor Mediated Neurite Outgrowth from PC-12 cells. Neuroscience Let., 199, 131 (1995)].

The compound SR57746A is reported to have nerve growth factor potentiating activity and is in clinical trials [see Fournier J, et al. Protective Effects of SR57746A in Central and Peripheral Models of Neurodegenerative Disorders in Rodents and Primates. Neuroscience, 55(3), 629–41, August 1993; U.S. Pat. Nos. 5,270,320 and 5,462, 945]. In addition, EP0372934, EP0459819 and U.S. Pat. No. 5,075,305 disclose substituted pyrimidines having NGF-like properties and its possible use in treating CNS degenerative diseases like Alzheimer's disease as well as peripheral neuropathies and other peripheral nervous system disorders.

SUMMARY OF THE INVENTION

We have now discovered a series of substituted pyrimidines that demonstrate NGF-like activity and/or enhancement of NGF activity in PC12 cells. The compounds stimulated both neurite outgrowth and choline acetyltransferase activity in in vitro experiments. Such activities are predictive for causing increased choline acetyltransferase activity in rat striatum and improving cognitative performance in animal models of age-induced working memory deficits by potentiating the activity of endogenous NGF in the brain. [see P. J. Middlemiss et al., AIT-082, A Unique Purine Derivative, Enhances Nerve Growth Factor Mediated Neurite Outgrowth from PC-12 cells. neuroscience Let., 199, 131 (1995); A. J. Galsky et al., Effect of AIT-082, a Purine Analog, on Working Memory in Normal and Aged Mice. pharmacol. Biochem. Behav., 47, 325 (1994); R. Morris, Developments of a Water-maze Procedure for Studying Spatial Learning in the Rat. J. Neurosci. Methods, 11, 47 (1984)].

DETAILED DESCRIPTION OF THE INVENTION

According to the present invention, there are provided novel compounds of Formula I:

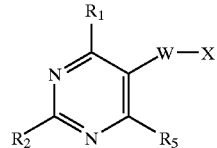

Formula I wherein
W is O, CH2, CH2CH2, OCH2 or CH2CH2CH2;
$R_1$ is pyrrolidino;
3-oxopiperidino;
4-oxopiperidino; or
NR4R5 wherein R4 and R5 are independently H, OH, C3-11alkenyl, C8-10aryl, C3-11alkynyl, dihydroxyC3-10alkyl, hydroxyC2-10alkyl, C2-6alkoxy, C6-10aryloxy, C8-10arylC1-6alkoxy, C1-6alkylthioC2-6alkyl, (C1-6alkyl)j(C3-9cycloalkyl)(CH2)q (wherein j is 0 or 1 and q is 0–6), (C1-6alkyl)j(C6-10aryl)(CH2)q (wherein j is 0 or 1 and q is 0–6), (C1-6alkyl)j(C4-9heterocycloalkyl)(CH2)q (wherein j and q are as above and the heterocyclic ring contains one heteroatom which is O, S or N), oxo(C3-8cycloalkyl)(CH2)q (wherein q is 0–6), hydroxy(CH2)p(C3-8cycloalkyl)(CH2)q (wherein p and q are independently 0–6), or C1-8alkyl, provided, however, that both R4 and R5 are not H, OH or C1-6alkyl, and when $R_2$ is H and W is O, neither R4 nor R5 is C1-6alkyl, wherein the C and N atoms of R4 and R5 may optionally be substituted with one or more substituents selected from the group consisting of:
OH;
halogen;
thio;
thio-oxo;
oxo;
C1-6alkyl;
C2-7alkenyl;
C2-7alkynyl;
C6-10aryl;
C6-10heteroaryl;
hydroxyC1-6alkyl;
dihydroxyC1-6alkyl;
C1-6alkoxy;
C1-6aryloxy;
C6-10heteroaryloxy;
hydroxyC1-6alkoxy;
C1-6alkoxyC1-6alkyl;
C6-10aryloxyC1-6alkyl;
C6-10heteroaryloxyC1-6alkyl;
C3-8cycloalkyl;
C6-10arylC1-6alkyl;
C6-10heteroarylC1-6alkyl;
C6-10arylC1-6alkoxy;
C6-10heteroarylC1-6alkoxy;
C1-6alkylcarbonylC1-6alkyl;
C6-10arylcarbonylC1-6alkyl;
carboxyC1-6alkyl;
C1-6alkoxycarbonylC1-6alkyl;
C6-10aryloxycarbonylC1-6alkyl;
C6-10arylC1-6alkyloxycarbonylC1-6alkyl;
cyanoC1-6alkyl;
C1-6alkylthioC1-6alkyl;
C1-6alkylsulfinylC1-6alkyl;
C1-6alkylsulfonylC1-6alkyl;
C6-10arylthioC1-6alkyl;
C6-10arylsulfinylC1-6alkyl;
C6-10arylsulfonylC1-6alkyl;
C6-10arylC1-6alkylthioC1-6alkyl;
C6-10arylC1-6alkylsulfinylC1-6alkyl;
C6-10arylC1-6alkylsulfonylC1-6alkyl;
C6-10heteroarylthioC1-6alkyl;
C6-10heteroarylsulfinylC1-6alkyl;
C6-10heteroarylsulfonylC1-6alkyl;
aziridino;
azetidino;
pyrrolidino;
piperidino;
heptamethyleneimino;
homopiperazino;
N-substituted homopiperazino (wherein the substituent may be C1-6alkyl, C6-10aryl, C6-10arylC1-6alkyl or C6-10heteroaryl);
piperazino;
N-substituted piperazino (wherein the substituent may be C1-6alkyl, C6-10aryl, C6-10arylC1-6alkyl or C6-10heteroaryl);
morpholino;
homomorpholino;
thiomorpholino;
aminoC1-6alkyl;
C1-6alkylaminoC1-6alkyl;
di(C1-6alkyl)aminoC1-6alkyl (wherein the alkyl groups may be the same or different);
C6-10arylaminoC1-6alkyl;
C6-10arylC1-6alkylaminoC1-6alkyl;
di(C6-10aryl)aminoC1-6alkyl (wherein the aryl groups may be the same or different;
di(C6-10arylC1-6aryl)aminoC1-6alkyl (wherein the arylalkyl groups may be the same or different);
R12C(O)C1-6alkyl (wherein R12 is aziridino, axetidino, pyrrolidino, piperidino, heptamethyleneimino, piperazino, homopiperazino, morpholino, homomorpholino, or thiomorpholino);
C(O)R6; (C(O)C(O)R6; C(S)R6; S(O)2R6; and C(NR11)R6 (wherein R11 is hydrogen, C1-6alkyl or C6-10aryl and R6 is H, C1-6alkyl, C6-10aryl, C6-10arylC1-6alkyl or C6-10heteroaryl);
$R_2$ is selected from the group consisting of:
H;
NH2, provided that when W is CH2, $R_2$ is NH2;
$R_2$ is H;
X is a C8-10 aryl ring or a C6-10 heteroaryl ring optionally substituted with one or more substituents Y selected from the group consisting of:
halogen;
C1-6 alkyl;
C2-7alkenyl;
C2-7alkynyl;
C6-10aryl;
C6-10heteroaryl;
OR;
NR8R10 (wherein R8 and R10 may be the same or different and are H, C1-6alkyl, C3-8cycloalkyl, C6-10aryl, or C8-10arylC1-6alkyl);
NROR;
C(O)NR9R10;
C(O)OR;

C(O)R;
NRC(O)NR9R10
NRC(O)R;
NRC(O)OR;
CR(OH)R;
OC(O)R;
S(O)nR wherein R is other than H and n is 0, 1 or 2;
NRS(O)mR wherein R is other than H and m is 1 or 2;
S(O)2NR9R10;
NO2;
CN;
CF3;
OCF3;
R is H, C1-6alkyl, C3-8cycloalkyl, C6-10aryl or C6-10arylC1-6alkyl; and pharmaceutically acceptable esters, amides, salts or solvates thereof.

The present invention includes all enantiomeric and diastereomeric forms of the compounds of Formula I either individually or admixed in any proportion.

The present invention further includes prodrugs and active metabolites of the compounds of Formula I. A prodrug includes any compound which, when administered to a mammal, is converted in whole or in part to a compound of Formula I. An active metabolite is a physiologically active compound (such as 5-(4-chlorophenoxy)-2,4-diaminopyrimidine) which results from the metabolism of a compound of Formula I, or a prodrug thereof, when such compound or prodrug is administered to a mammal.

The compounds of Formula I above and their pharmaceutically acceptable esters, amides, salts or solvates are sometimes hereinafter referred to as "the compounds according to the invention".

By "alkyl" is meant straight or branched chain alkyl. The alkyl groups may be optionally substituted with hydroxy, alkoxy, amino or halogen.

By "aryl" is meant an aromatic ring such as phenyl or naphthyl. The aryl groups may be optionally substituted with hydroxy, alkoxy, amino or halogen.

By "heteroaryl" is meant a ring containing 1 to 4 heteroatoms selected from the group consisting of N, O and S.

By "halogen" is meant F, Cl, Br or I.

Preferred compounds included in the present invention are more particularly defined by the following Formulas IA–IC:

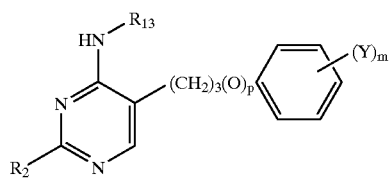

Formula IA wherein a and b are 0 or 1 and a+b−1; m is 0–2; $R_2$ is H or NH2, provided that when a=1, $R_2$ is NH2; $R_{13}$ is phenyl, benzyl or cyclohexyl substituted with 0, 1 or 2 hydroxyl groups; Y is any substituent of X as hereinbefore defined; and pharmaceutically acceptable esters, amides, salts or solvates thereof.

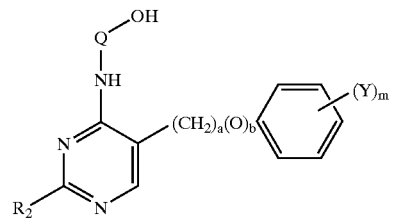

Formula IB

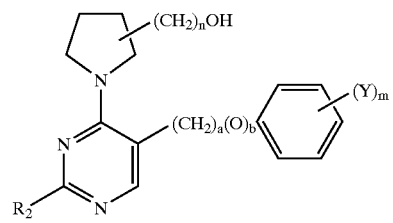

Formula IC wherein a and b are 0 or 1 and a+b=1; m is 0–2; n is 0–3; $R_2$ is H or NH2; Y is any substituent of X as hereinbefore defined; and Q is C2-10alkyl optionally substituted with one or more OH; and pharmaceutically acceptable esters, amides, salts or solvates thereof.

Preferred compounds of Formula I are those wherein W is O or CH2 and X is substituted phenyl; and pharmaceutically acceptable esters, amides, salts or solvates thereof.

Most preferred compounds of Formula I are those wherein $R_1$ is 4-oxocyclohexylamino, trans-4-hydroxycyclohexylamino, 4-hydroxyanilino, or 4-(2-hydroxyethylamino); W is oxygen; X is phenyl optionally substituted with 4-chloro, 2,4 dichloro, 4-bromo, 2-fluoro-4-chloro, 2-chloro-4-fluoro, 2-methyl-4-chloro, 4-methyl, or 4-ethyl; and $R_2$ is NH2; and pharmaceutically acceptable esters, amides, salts or solvates thereof.

Specifically preferred compounds of Formula I are:

2-Amino-4-(oxocyclohexylamino)-5-(4-chlorophenoxy)pyrimidine

2-Amino-4-(oxocyclohexylamino)-5-(2,4-dichlorophenoxy)pyrimidine

2-Amino-4-(oxocyclohexylamino)-5-(4-bromophenoxy)pyrimidine

2-Amino-4-(oxocyclohexylamino)-5-(2-fluoro-4-(chlorophenoxy)pyrimidine

2-Amino-4-(oxocyclohexylamino)-5-(2-chloro-4-(fluorophenoxy)pyrimidine

2-Amino-4-(oxocyclohexylamino)-5-(2-methyl-4-(chlorophenoxy)pyrimidine

2-Amino-4-(oxocyclohexylamino)-5-(4-methylphenoxy)pyrimidine

2-Amino-4-(oxocyclohexylamino)-5-(4-ethylphenoxy)piperimidine

2-Amino-4-(hydroxycyclohexylamino)-5-(4-chlorophenoxy)pyrimidine

2-Amino-4-(hydroxycyclohexylamino)-5-(2,4-dichlorophenoxy)pyrimidine

2-Amino-4-(hydroxycyclohexylamino)-5-(4-bromophenoxy)pyrimidine

2-Amino-4-(hydroxycyclohexylamino)-5-(2-fluoro-4-(chlorophenoxy)pyrimidine

2-Amino-4-(hydroxycyclohexylamino)-5-(2-chloro-4-(fluorophenoxy)pyrimidine

2-Amino-4-(hydroxycyclohexylamino)-5-(2-methyl-4-(chlorophenoxy)pyrimidine

2-Amino-4-(hydroxycyclohexylamino)-5-(4-methylphenoxy)pyrimidine

2-Amino-4-(hydroxycyclohexylamino)-5-(4-ethylphenoxy)pyrimidine
2-Amino-4-(hydroxyanilino)-5-(4-chlorophenoxy)pyrimidine
2-Amino-4-(hydroxyanilino)-5-(2,4-dichlorophenoxy)pyrimidine
2-Amino-4-(hydroxyanilino)-5-(4-bromophenoxy)pyrimidine
2-Amino-4-(hydroxyanilino)-5-(2-fluoro-4-(chlorophenoxy)pyrimidine
2-Amino-4-(hydroxyanilino)-5-(2-chloro-4-(fluorophenoxy)pyrimidine
2-Amino-4-(hydroxyanilino)-5-(2-methyl-4-(chlorophenoxy)pyrimidine
2-Amino-4-(hydroxyanilino)-5-(4-methylphenoxy)pyrimidine
2-Amino-4-(hydroxyanilino)-5-(4-ethylphenoxy)pyrimidine
2-Amino-4-(2-hydroxyethylamino)-5-(4-chlorophenoxy)pyrimidine
2-Amino-4-(2-hydroxyethylamino)-5-(2,4-dichlorophenoxy)pyrimidine
2-Amino-4-(2-hydroxyethylamino)-5-(4-bromophenoxy)pyrimidine
2-Amino-4-(2-hydroxyethylamino)-5-(2-fluoro-4-chlorophenoxy)pyrimidine
2-Amino-4-(2-hydroxyethylamino)-5-(2-chloro-4-fluorophenoxy)pyrimidine
2-Amino-4-(2-hydroxyethylamino)-5-(2-methyl-4-chlorophenoxy)pyrimidine
2-Amino-4-(2-hydroxyethylamino)-5-(4-methylphenoxy)pyrimidine
2-Amino-4-(2-hydroxyethylamino)-5-(4-ethylphenoxy)pyrimidine
2-Amino-5-(4-chlorophenoxy)-4-(cyclohexylamino)pyrimidine
2-Amino-5-(4-chlorophenoxy)-4-(trans-3-hydroxycyclohexylamino)pyrimidine
2-Amino-5-(4-chlorophenoxy)-4-(trans-2-hydroxycyclohexylamino)pyrimidine
2-Amino-5-(4-chlorophenoxy)-4-(cis-4-hydroxycyclohexylamino)pyrimidine
2-Amino-5-(4-chlorophenoxy)-4-(cis-3-hydroxycyclohexylamino)pyrimidine
2-Amino-5-(4-chlorophenoxy)-4-(cis-2-hydroxycyclohexylamino)pyrimidine
2-Amino-5-(4-chlorophenoxy)-4-(3-oxocyclohexylamino)pyrimidine
2-Amino-5-(4-chlorophenoxy)-4-(2-oxocyclohexylamino)pyrimidine
2-Amino-5-(4-chlorophenoxy)-4-(trans-4-(hydroxymethyl)cyclohexylamino)pyrimidine
2-Amino-5-(4-chlorophenoxy)-4-(trans-3-(hydroxymethyl)cyclohexylamino)pyrimidine
2-Amino-5-(4-chlorophenoxy)-4-(trans-2-(hydroxymethyl)cyclohexylamino)pyrimidine
2-Amino-5-(4-chlorophenoxy)-4-(cis-4-(hydroxymethyl)cyclohexylamino)pyrimidine
2-Amino-5-(4-chlorophenoxy)-4-(cis-3-(hydroxymethyl)cyclohexylamino)pyrimidine
2-Amino-5-(4-chlorophenoxy)-4-(cis-2-(hydroxymethyl)cyclohexylamino)pyrimidine
2-Amino-5-(4-chlorophenoxy)-4-(trans-4-(2-hydroxyethyl)cyclohexylamino)pyrimidine
2-Amino-5-(4-chlorophenoxy)-4-(trans-3-(2-hydroxyethyl)cyclohexylamino)pyrimidine
2-Amino-5-(4-chlorophenoxy)-4-(trans-2-(2-hydroxyethyl)cyclohexylamino)pyrimidine
2-Amino-5-(4-chlorophenoxy)-4-(cis-4-(2-hydroxyethyl)cyclohexylamino)pyrimidine
2-Amino-5-(4-chlorophenoxy)-4-(cis-3-(2-hydroxyethyl)cyclohexylamino)pyrimidine
2-Amino-5-(4-chlorophenoxy)-4-(cis-2-(2-hydroxyethyl)cyclohexylamino)pyrimidine
2-Amino-5-(4-chlorophenoxy)-4-(trans-4-hydroxycyclohexylmethylamino)pyrimidine
2-Amino-5-(4-chlorophenoxy)-4-(trans-3-hydroxycyclohexylmethylamino)pyrimidine
2-Amino-5-(4-chlorophenoxy)-4-(trans-2-hydroxycyclohexylmethylamino)pyrimidine
2-Amino-5-(4-chlorophenoxy)-4-(cis-4-hydroxycyclohexylmethylamino)pyrimidine
2-Amino-5-(4-chlorophenoxy)-4-(cis-3-hydroxycyclohexylmethylamino)pyrimidine
2-Amino-5-(4-chlorophenoxy)-4-(cis-2-hydroxycyclohexylmethylamino)pyrimidine
2-Amino-5-(4-chlorophenoxy)-4-(trans-3-hydroxycyclopentylamino)pyrimidine
2-Amino-5-(4-chlorophenoxy)-4-(trans-2-hydroxycyclopentylamino)pyrimidine
2-Amino-5-(4-chlorophenoxy)-4-(cis-3-hydroxycyclopentylamino)pyrimidine
2-Amino-5-(4-chlorophenoxy)-4-(cis-2-hydroxycyclopentylamino)pyrimidine
2-Amino-5-(4-chlorophenoxy)-4-(3-oxocyclopentylamino)pyrimidine
2-Amino-5-(4-chlorophenoxy)-4-(2-oxocyclopentylamino)pyrimidine
2-Amino-5-(4-chlorophenoxy)-4-(trans-3-(hydroxymethyl)cyclopentylamino)pyrimidine
2-Amino-5-(4-chlorophenoxy)-4-(trans-2-(hydroxymethyl)cyclopentylamino)pyrimidine
2-Amino-5-(4-chlorophenoxy)-4-(cis-3-(hydroxymethyl)cyclopentylamino)pyrimidine
2-Amino-5-(4-chlorophenoxy)-4-(cis-2-(hydroxymethyl)cyclopentylamino)pyrimidine
2-Amino-5-(4-chlorophenoxy)-4-(trans-3-(2-hydroxyethyl)cyclopentylamino)pyrimidine
2-Amino-5-(4-chlorophenoxy)-4-(trans-2-(2-hydroxyethyl)cyclopentylamino)pyrimidine
2-Amino-5-(4-chlorophenoxy)-4-(cis-3-(2-hydroxyethyl)cyclopentylamino)pyrimidine
2-Amino-5-(4-chlorophenoxy)-4-(cis-2-(2-hydroxyethyl)cyclopentylamino)pyrimidine
2-Amino-5-(4-chlorophenoxy)-4-(trans-3-hydroxycyclopentylmethylamino)pyrimidine
2-Amino-5-(4-chlorophenoxy)-4-(trans-2-hydroxycyclopentylmethylamino)pyrimidine
2-Amino-5-(4-chlorophenoxy)-4-(cis-3-hydroxycyclopentylmethylamino)pyrimidine
2-Amino-5-(4-chlorophenoxy)-4-(cis-2-hydroxycyclopentylmethylamino)pyrimidine
2-Amino-5-(4-chlorophenoxy)-4-(trans-2-(hydroxymethyl)cyclobutylmethylamino)pyrimidine
2-Amino-5-(4-chlorophenoxy)-4-(trans-3-(hydroxymethyl)cyclobutylmethylamino)pyrimidine
2-Amino-5-(4-chlorophenoxy)-4-(cis-2-(hydroxymethyl)cyclobutylmethylamino)pyrimidine
2-Amino-5-(4-chlorophenoxy)-4-(cis-3-(hydroxymethyl)cyclobutylmethylamino)pyrimidine
2-Amino-5-(4-chlorophenoxy)-4-(trans-2-hydroxycyclobutylmethylamino)pyrimidine
2-Amino-5-(4-chlorophenoxy)-4-(trans-3-hydroxycyclobutylmethylamino)pyrimidine
2-Amino-5-(4-chlorophenoxy)-4-(cis-2-hydroxycyclobutylmethylamino)pyrimidine 2-Amino-5-(4-chlorophenoxy)-4-(cis-3-hydroxycyclobutylmethylamino)pyrimidine
2-Amino-5-(4-chlorophenoxy)-4-(trans-2-hydroxymethyl)cyclopropylmethylamino)pyrimidine
2-Amino-5-(4-chlorophenoxy)-4-(cis-2-(hydroxymethyl)cyclopropylmethylamino)pyrimidine
2-Amino-5-(4-chlorophenoxy)-4-(1-hydroxycyclopropylmethylamino)pyrimidine
2-Amino-5-(4-chlorophenoxy)-4-(1-hydroxycyclobutylmethylamino)pyrimidine
2-Amino-5-(4-chlorophenoxy)-4-(1-hydroxycyclopentylmethylamino)pyrimidine
2-Amino-5-(4-chlorophenoxy)-4-(1-hydroxycyclohexylmethylamino)pyrimidine
2-Amino-5-(4-chlorophenoxy)-4-(3-hydroxypropylamino)pyrimidine
2-Amino-5-(4-chlorophenoxy)-4-(4-hydroxybutylamino)pyrimidine
2-Amino-5-(4-chlorophenoxy)-4-(5-hydroxypentylamino)pyrimidine
2-Amino-5-(4-chlorophenoxy)-4-(6-hydroxyhexylamino)pyrimidine
2-Amino-5-(4-chlorophenoxy)-4-(2-hydroxy-1-methyl)ethylamino))pyrimidine
2-Amino-5-(4-chlorophenoxy)-4-(1,1-dimethyl-2-hydroxy)ethylamino))pyrimidine
2-Amino-5-(4-chlorophenoxy)-4-(1-hydroxymethyl-2-hydroxy(ethylamino))pyrimidine
2-Amino-5-(4-chlorophenoxy)-4-(2-hydroxy-1-hydroxymethyl-1-methyl(ethylamino))pyrimidine
2-Amino-5-(4-chlorophenoxy)-4-(tris(hydroxymethyl)methylamino)pyrimidine
2-Amino-5-(4-chlorophenoxy)-4-(2,3-dihydroxypropylamino)pyrimidine
2-Amino-5-(4-chlorophenoxy)-4-(3,4-dihydroxylbutylamino)pyrimidine
2-Amino-5-(4-chlorophenoxy)-4-(bis(2-hydroxyethyl)amino)pyrimidine
2-Amino-5-(4-chlorophenoxy)-4-(bis(3-hydroxypropyl)amino)pyrimidine
2-Amino-5-(4-chlorophenoxy)-4-(trans-4-hydroxycyclohexylamino)-6-(trifluoromethyl)pyrimidine
2-Amino-5-(4-chlorophenoxy)-4-(3-hydroxypyrrolidino)pyrimidine
2-Amino-5-(4-chlorophenoxy)-4-(2-hydroxymethylpyrrolidino)pyrimidine
2-Amino-5-(4-chlorophenoxy)-4-(2-hydroxyethylpyrrolidino)pyrimidine
2-Amino-5-(4-chlorophenoxy)-4-(3-hydroxymethylpyrrolidino)pyrimidine
2-Amino-5-(4-chlorophenoxy)-4-(3-(2-hydroxyethyl)pyrrolidino)pyrimidine
5-(4-Chlorophenoxy)-4-(trans-4-hydroxycyclohexylamino)pyrimidine
5-(4-Chlorophenoxy)-4-(cis-4-hydroxycyclohexylamino)pyrimidine
5-(4-Chlorophenoxy)-4-(cis-3-hydroxycyclohexylamino)pyrimidine
5-(4-Chlorophenoxy)-4-(4-oxocyclohexylamino)pyrimidine
5-(4-Chlorophenoxy)-4-(trans-4-(hydroxymethyl)cyclohexylamino)pyrimidine
5-(4-Chlorophenoxy)-4-(trans-3-(hydroxymethyl)cyclohexylamino)pyrimidine
5-(4-Chlorophenoxy)-4-(trans-3-hydroxycyclopentylamino)pyrimidine
5-(4-Chlorophenoxy)-4-(trans-2-hydroxycyclopentylamino)pyrimidine
5-(4-Chlorophenoxy)-4-(trans-3-(hydroxymethyl)cyclopentylamino)pyrimidine
5-(4-Chlorophenoxy)-4-(trans-2-(hydroxymethyl)cyclopentylamino)pyrimidine
5-(4-Chlorophenoxy)-4-(trans-2-(hydroxymethyl)cyclopropylamino)pyrimidine
5-(4-Chlorophenoxy)-4-(2-hydroxyethylamino)pyrimidine
5-(4-Ethylphenoxy)-4-(trans-4-hydroxycyclohexylamino)pyrimidine
5-(2,4-Dichlorophenoxy)-4-(trans-4-hydroxycyclohexylamino)pyrimidine
4-(trans-4-Hydroxycyclohexylamino)-5-(4-trifluoromethylphenoxy)pyrimidine
5-(4-Chloro-2-fluorophenoxy)-4-(trans-4-hydroxycyclohexylamino)pyrimidine
2-Amino-5-(2,4-dichlorophenoxy)-4-(trans-4-hydroxycyclohexylamino)pyrimidine
2-Amino-5-(4-chloro-2-methylphenoxy)-4-(trans-4-hydroxycyclohexylamino)pyrimidine
2-Amino-5-(2-chlorophenoxy)-4-(trans-4-hydroxycyclohexylamino)pyrimidine
2-Amino-5-(4-fluorophenoxy)-4-(trans-4-hydroxycyclohexylamino)pyrimidine
2-Amino-4-(trans-4-hydroxycyclohexylamino)-5-(4-trifluoromethylphenoxy)pyrimidine
2-Amino-4-(trans-4-hydroxycyclohexylamino)-5-(4-methylphenoxy)pyrimidine
2-Amino-4-(trans-4-hydroxycyclohexylamino)-5-(2-methylphenoxy))pyrimidine
2-Amino-4-(trans-4-hydroxycyclohexylamino)-5-(4-isopropylphenoxy)pyrimidine
2-Amino-5-(4-butylphenoxy)-4-(trans-4-hydroxycyclohexylamino)pyrimidine
2-Amino-4-(trans-4-hydroxycyclohexylamino)-5-(4-methoxyphenoxy)pyrimidine
2-Amino-4-(trans-4-hydroxycyclohexylamino)-5-(2-methoxyphenoxy)pyrimidine
2-Amino-4-(trans-4-hydroxycyclohexylamino)-5-(4-trifluoromethoxy)phenoxy)pyrimidine
2-Amino-5-(2,3-difluorophenoxy)-4-(trans-4-hydroxycyclohexylamino)pyrimidine
2-Amino-5-(2,4-difluorophenoxy)-4-(trans-4-hydroxycyclohexylamino)pyrimidine
2-Amino-5-(2,6-difluorophenoxy)-4-(trans-4-hydroxycyclohexylamino)pyrimidine
2-Amino-5-(4-chloro-2-fluorophenoxy)-4-(trans-4-hydroxycyclohexylamino)pyrimidine
2-Amino-5-(2-chloro-4-ethylphenoxy)-4-(trans-4-hydroxycyclohexylamino)pyrimidine
2-Amino-5-(2,4,6-trichlorophenoxy)-4-(trans-4-hydroxycyclohexylamino)pyrimidine
2-Amino-4-(trans-4-hydroxycyclohexylamino)-5-(4-methylbenzyl)pyrimidine
2-Amino-5-(4-chlorobenzyl)-4-(trans-4-hydroxycyclohexylamino)pyrimidine
2-Amino-4-(trans-4-hydroxycyclohexylamino)-5-(4-trifluoromethylbenzyl)pyrimidine
2-Amino-4-(trans-4-hydroxycyclohexylamino)-5-(isopropylbenzyl)pyrimidine
2-Amino-5-(4-chlorobenzyl)-4-(4-oxopiperidino)pyrimidine
2-Amino-5-(4-bromobenzyl)-4-(4-oxopiperidino)pyrimidine
2-Amino-4-(4-oxopiperidino)-5-(4-trifluoromethylbenzyl)pyrimidine
2-Amino-5-(4-methylbenzyl)-4-(4-oxopiperidino)pyrimidine 2-Amino-5-(4-ethylbenzyl)-4-(4-oxopiperidino)pyrimidine
2-Amino-5-(4-chlorobenzyl)-4-(3-oxopiperidino)pyrimidine
2-Amino-5-(4-bromobenzyl)-4-(3-oxopiperidino)pyrimidine
2-Amino-4-(4-oxopiperidino)-5-(3-trifluoromethylbenzyl)pyrimidine
2-Amino-5-(4-methylbenzyl)-4-(3-oxopiperidino)pyrimidine
2-Amino-5-(4-ethylbenzyl)-4-(3-oxopiperidino)pyrimidine
2-Amino-5-(2,4-dichlorobenzyl)-4-(4-oxopiperidino)pyrimidine
2-Amino-5-(2-chloro-4-bromobenzyl)-4-(4-oxopiperidino)pyrimidine
2-Amino-5-(2-chloro-4-trifluoromethylbenzyl)-4-(4-oxopiperidino)pyrimidine
2-Amino-5-(2-chloro-4-methylbenzyl)-4-(4-oxopiperidino)pyrimidine
2-Amino-5-(2-chloro-4-ethylbenzyl)-4-(4-oxopiperidino)pyrimidine
2-Amino-5-(2,4-dichlorobenzyl)-4-(3-oxopiperidino)pyrimidine
2-Amino-5-(2-chloro-4-bromobenzyl)-4-(3-oxopiperidino)pyrimidine
2-Amino-5-(2-chloro-4-trifluoromethylbenzyl)-4-(3-oxopiperidino)pyrimidine
2-Amino-5-(2-chloro-4-methylbenzyl)-4-(3-oxopiperidino)pyrimidine
2-Amino-5-(2-chloro-4-ethylbenzyl)-4-(3-oxopiperidino)pyrimidine
2-Amino-5-(4-chlorophenethyl)-4-(trans-4-hydroxycyclohexylamino)pyrimidine
2-Amino-5-(4-chlorobenzyloxy)-4-(trans-4-hydroxycyclohexylamino)pyrimidine
2-Amino-5-(4-chlorophenoxy)-4-(4-hydroxy-2-methylanilino)pyrimidine
4-(4-acetoxyanilino)-2-amino-5-(4-chlorophenoxy)pyrimidine
2-Amino-5-(4-chlorophenoxy)-4-(2-(2-proprionyloxyethoxy)ethylamino)pyrimidine hydrochloride
2-Amino-5-(4-chlorophenoxy)-4-(4-hydroxy-2-chloroanilino)pyrimidine
2-Amino-4-(2-hydroxyethoxyamino)-5-(4-chlorophenyloxy)pyrimidine
and pharmaceutically acceptable esters, amides, salts or solvates thereof.

In one aspect of the invention there is provided the compounds according to the invention for use in medical therapy, particularly for the treatment of neurodegenerative or neurological disorders of the central or peripheral nervous systems.

Examples of nervous system disorders which may be treated in accordance with the invention include dementing disorders such as age-related senility, senile dementia or Age Related Mental Impairment (ARMI), cerebral ataxia, Parkinson's disease, Alzheimer's disease, peripheral neuropathy, cognitive disorders secondary to stroke or trauma and attention-deficit hyperactivity disorder. In addition, nerve injuries, for example, spinal cord injuries, that require neuroregeneration may also be treated in accordance with the invention.

In a further aspect of the present invention there is included:
a) A method for the treatment of neurodegenerative or neurological disorders of the central or peripheral nervous systems which comprises treating the subject e.g., a mammal, such as a human, with a therapeutically effective amount of a compound according to the invention.
b) Use of a compound according to the invention in the manufacture of a medicament for the treatment of any of the above-mentioned disorders.

Examples of pharmaceutically acceptable salts of the compounds according to the invention include acid addition salts. However, salts of non-pharmaceutically acceptable acids may be of utility in the preparation and purification of the compounds of the invention.

Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethansulfonic, p-toluenesulfonic, benzenesulfonic and isethionic acids.

The compounds according to the invention and pharmaceutically acceptable esters, amides, esters, amides, salts or solvates thereof may be employed in combination with other therapeutic agents for the treatment of the above disorders. Examples of such further therapeutic agents include Cognex, Aricept and other agents (e.g., acetylcholine esterase inhibitors, muscarinic or nicotinic receptor agonists, MAO inhibitors) that are effective for the treatment of neurodegenerative or neurological disorders of the central or peripheral nervous systems. The component compounds of such combination therapy may be administered simultaneously in either separate or combines formulations, or at different times, e.g., sequentially such that a combined effect is achieved.

While it is possible for compounds according to the invention to be administered as the raw chemical, it is preferable to present them as a pharmaceutical formulation. The formulations of the present invention comprise a compound of Formula I, as above defined, or a pharmaceutically acceptable ester, amide, salt or solvate thereof, together with one or more pharmaceutically acceptable carriers therefor and optionally other therapeutic ingredients. The carrier(s) must be acceptable in the sense of being compatible with the other ingredients of the formulation and not deleterious to the recipient thereof.

The formulations include those suitable for oral, parenteral (including subcutaneous, transdermal, intradermal, intramuscular and intravenous), rectal and topical (including dermal, buccal and sublingual) administration although the most suitable route may depend upon, for example, the condition and disorder of the recipient. The formulations may conveniently be presented in unit dosage form and may be prepared by any of the methods well know in the art of pharmacy. All methods include the step of bringing into association a compound of Formula I or a pharmaceutically acceptable ester, amide, salt or solvate thereof (active ingredient) with the carrier which constitutes one or more accessory ingredients. In general the formulations are prepared by uniformly and intimately bringing into association the active ingredients with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion, or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacterioistats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophillised) condition requiring only the addition of the sterile liquid carrier, for example, water-for-injection, immediately prior to use. Extemporaneous injection solutions and suspensions may be prepared from sterile powders, granules and tablets of the kind previously described.

Formulations suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 35%, preferably about 3% to 15%. As one particular possibility, the active compound may be delivered from the patch by electrotransport or iontophoresis, as generally described in Pharmaceutical Res., 3(6), 318 (1986).

Formulations for rectal administration may be presented as suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

Tablets or other forms of presentation in discrete units may conveniently contain an amount of compound of the Formula I which is effective for each of the above-mentioned indications at such dosage or as a multiple of the same, for instance, units containing 5 mg to 500 mg, usually between 10 mg to 250 mg.

For the above-mentioned conditions and disorders, the compounds of the Formula I are preferably administered orally or by injection (intraparenteral or subcutaneous). The precise amount of compound administered to a patient will be the responsibility of the attendant physician. However, the dose employed will depend on a number of factors, including the age and sex of the patient, the precise disorder being treated, and its severity. Also the route of administration is likely to vary depending on the condition and its severity.

For each of the above-mentioned indications the compounds of the Formula I may be administered orally. The dose range for adult humans is generally from about 10 to 4000 mg/day and preferably from about 100 to 1000 mg/day. It may be advantageous to administer an initial dose of 200 to 2000 mg the first day then a lower dose of 100 to 1000 mg on subsequent days.

For each of the above-mentioned indications, the compounds according to the invention may be administered by injection at a dose of from about 1 to 1000 mg/day, and preferably from about 5 to 1000 mg/day.

The present invention further includes processes for the preparation of compounds of Formula (I) and esters, amides, salts or solvates thereof. The compounds of Formula (I) and their esters, amides, salts and solvates may be prepared in accordance with the present invention by the methods hereinafter describes, or in any manner known in the art for the preparation of compounds of analogous structure.

By way of illustration, the compounds, esters, amides, salts and solvates of Formula (I) may be prepared by a process which comprises:

reacting a compound of Formula (II)

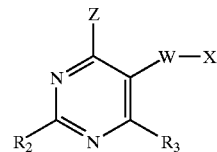

Formula II wherein $R_2$, $R_3$, W and X are as hereinbefore defined and Z is a leaving group, with an amine NR'R" (wherein R' and R" are as defined for $R_1$) or a suitable derivative thereof. Suitable leaving groups include halogens such as chlorine. The reaction is carried out in an organic solvent (e.g., ethanol, propanol, N,N-dimethylformamide) at a temperature of approximately 20° C. to approximately 120° C. The compound of Formula (II) may be isolated and purified prior to reaction with an amine NR'R" or may be used in situ.

Compounds of Formula (II) wherein Z is a halogen atom can be prepared from compounds of

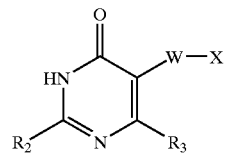

Formula III wherein $R_2$, $R_3$, W and X are as hereinbefore defined by reaction with a halogenating agent (e.g., Vilsmeier reagent (e.g., oxalyl chloride and N,N-dimethylformamide, oxalyl chloride and N,N-diisopropylformamide), phosphorous oxychloride, phosphorous pentachloride, thionyl chloride) in a suitable organic solvent (e.g., dichloromethane, 1,2-dichlorethane, toluene, N,N-dimethlyformamide) at a temperature of approximately 40° C. to approximately 100° C.

Compounds of Formula (III) can be prepared from compounds of Formula (IV)

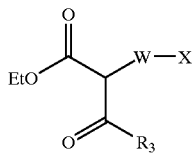

Formula IV wherein $R_3$, W and X are as hereinbefore defined by reaction of an alkaline earth salt of (IV) with formamidine or a derivative of formamidine (e.g., guanidine, thiourea, 2-ethyl-2-thiopseudourea) in a suitable organic solvent (e.g., ethanol, methanol, 2-propanol, tert-butanol, tetrahydrofuran) at a temperature of approximately 60° C. to the reflux temperature.

Compounds of Formula (IV) can be prepared from compounds of Formula (V)

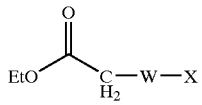

Formula V wherein W and X are as hereinbefore defined by reaction with an ester (e.g., ethyl formate, ethyl acetate, ethyl benzoate, ethyl trifluoroacetate) and a strong base (e.g., sodium hydride, potassium hydride, potassium tert-butoxide, sodium metal, lithium diisopropylamine) in a suitable organic solvent (e.g., tetrahydrofuran, ether, toluene) at a temperature of approximately 0° C. to approximately 40° C.

Compounds of Formula (V) can be prepared by various methods known in the art or are available from commercial sources.

Compounds of Formula (III) wherein $R_2$ is H can also be prepared from compounds of Formula (VI)

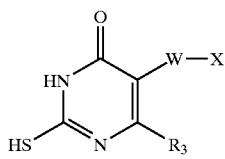

Formula VI wherein $R_3$, W and X are as hereinbefore defined, by reaction with Raney Ni in a suitable solvent (e.g., ethanol, methanol, 2-methoxyethanol) at a temperature of approximately 60° C. to approximately 100° C.

Specifically preferred intermediate compounds for synthesis of the above-listed specifically preferred compounds of Formula (I) are:
5-(Phenoxy)isocytosine
5-(4-Methylphenoxy)isocytosine
5-(4-Chlorophenoxy)isocytosine
5-(4-Chlorophenoxy)-2-(mercapto)pyrimidin-4-(3H)-one
5-(4-Chlorobenzyl)isocytosine
5-(4-Methylbenzyl)isocytosine
5-(4-Chlorophenoxy)pyrimidin-4(3H)-one
5-(4-Ethylphenoxy)isocytosine
5-(4-Chloro-2-fluorophenoxy)isocytosine
5-(2,4-Dichlorophenoxy)isocytosine
5-(4-Bromophenoxy)isocytosine
5-(4-Trifluoromethylphenoxy)isocytosine
5-(2,4-Difluorophenoxy)isocytosine
5-(3,4-Difluorophenoxy)isocytosine
5-(4-Chlorophenoxy)-2-(diisopropylaminomethyleneamino)pyrimidin-4(3H)-one
5-(4-Chlorophenoxy)-2-(diisopropylaminomethyleneamino)-4-(trans-4-hydroxycyclohexylamino)pyrimidine
4-Chloro-5-(4-chlorophenoxy)-2-(diisopropylaminomethyleneamino)pyrimidine
5-(2,4-dichlorobenzyl)isocytosine
5-(2,4,6-trichlorobenzyl)isocytosine
5-(2,4,6-trichlorophenoxy)isocytosine Esters and amides of compounds of Formual (I) can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C.

Salts of the compounds of Formula (I) can be made from the free base form by reaction with the appropriate acid.

The following Examples illustrate the present invention but should not be construed as a limitation to the scope thereof.

Example 1

Preparation of 5-(4-chlorophenoxy)isocytosine

A solution of 4-chlorophenoxyacetic acid (Aldrich) (18.62 g, 99.8 mmoles) and concentrated sulfuric acid (Fisher) (2.5 mL) in ethanol (170 mL) was refluxed with stirring under a DRIERITE tube for 96 hours. The reaction solution was cooled in an ice-bath, and the volatiles were removed by spin evaporation in vacuo to a volume of about 100 mL. The liquid was dissolved in dichloromethane (225 mL) and washed with a solution of 5% aqueous sodium bicarbonate (4×100 mL) and finally with brine (1×50 mL). The solution was dried over sodium sulfate and spin evaporated in vacuo to give 19.97 g (93% yield) of ethyl 4-chlorophenoxyacetate as an amber liquid.

A solution of the ethyl 4-chlorophenoxyacetate (19.90 g, 92.7 mmoles) and ethyl formate (Acros) (30 mL, 371 mmoles) in tetrahydrofuran (100 mL) was added dropwise to a stirred dispersion of sodium hydride (60% dispersion in mineral oil) (Aldrich) (5.31 g, 132.7 mmoles) in tetrahydrofuran (50 mL). After 30 minutes, when about 60% of the solution had been added, the reaction was cooled with an ice-bath to slow the reaction. After a total of 1 hour addition was complete, the addition funnel was rinsed with tetrahydrofuran (15 mL), and the reaction mixture was stirred at ambient temperature for 16 hours. The solution was cooled on an ice-bath. The volatiles were removed by spin evaporation in vacuo to give the sodium salt of ethyl 2-formyl-2-(4-chlorophenoxy)acetate as a syrup that solidified after several hours. The solid was largely dissolved in ethanol (100 mL) and combined with a white mixture prepared from mixing sodium methoxide (Aldrich) (6.04 g, 106.2 mmoles) and guanidine carbonate (Aldrich) (10.05 g, 55.7 mmoles) in ethanol (75 mL). The reaction mixture was refluxed with stirring for 6 hours. The reaction mixture was cooled on an ice-bath. The volatiles were removed by spin evaporation in vacuo to give a semi-solid residue, which was dissolved in cold water to a volume of 500 mL. The solution was vigorously stirred and acidified to pH 5 with acetic acid (15 mL), which was added in 3 equal portions. The cream colored mixture was stirred for 2 hours. The solid was collected, washed extensively with water (750 mL), and vacuum suction air dried to give the crude solid. The solid was heated with stirring in ethanol to a final volume of 200 mL. The cooled mixture was collected, washed with ethanol and dried to give 16.83 g (76% yield) of 5-(4-chlorophenoxy)isocytosine as a white solid, mp 245° C.

Example 2
Preparation of 4-chloro-5-(4-chlorophenoxy)-2-(diisopropylaminomethyleneamino)pyrimidine Diisopropylformamide (Aldrich) (92.56 g, 0.716 mole) and dichloromethane (mL) were combined in a 5 L three-neck round bottom flask equipped with an air stirrer, reflux condenser, thermometer and dropping funnel with drying tube. Neat oxalyl chloride (Aldrich) (100 g, 0.788 mole) was slowly added over 3 hours during which the reaction temperature remained at 22–25° C. Solid 5-(4-chlorophenoxy) isocytosine (65.68 g, 0.276 mole) was added, and the mixture was refluxed for 2.5 hours to give a clear burgundy colored solution. After cooling to ambient temperature, a cold solution of saturated aqueous sodium bicarbonate solution (1.1 L) was added in 15–20 mL increments with rapid stirring. The organic phase was separated, washed with water (1×1 L), saturated brine (1×1 L) and dried over sodium sulfate. This solution was filtered through a bed of Silica Gel (150 g; 4×26 cm) in dichloromethane, and the bed was rinsed with additional dichloromethane (500 mL). The combined filtrates and washings were evaporated in vacuo to a thick oil, which was immediately stirred with hexanes (1.5 L) to give a flocculent white solid. The solids were collected, rinsed with hexanes and dried in vacuo at ambient temperature to give 77.3 g (76% yield) of 4-chloro-5-(4-chlorophenoxy)-2-(diisopropylaminomethyleneamino) pyrimidine as white needles, mp 135–136° C.

Example 3
Preparation of 2-amino-5-(4-chlorophenoxy)-4-(trans-4-hydroxycyclohexylamino)pyrimidine 4-Chloro-5-(4-chlorophenoxy)-2-(diisopropylaminomethyleneamino)pyrimidine (3.68 g, 0.01 mole) and trans-4-aminocyclohexanol hydrochloride (5.31 g, 0.035 mole) were combined in absolute ethanol (25 mL). Triethylamine (7.08 g, 0.07 mole) was added, and the mixture was refluxed with stirring for 56 hours when thin layer chromatography confirmed the absence of the starting pyrimidine. The mixture was cooled slightly, concentrated hydrochloric acid (5 mL) was added and reflux was resumed for an additional 2 hours. The mixture was spin evaporated in vacuo. The oily residue was dissolved in water (200 mL) and extracted with dichloromethane (2×200 mL). The aqueous phase was basified with 2 M sodium hydroxide to pH 9, and the gummy residue that precipitated was dissolved in dichloromethane (100 mL). The aqueous phase was back washed with dichloromethane (100 mL), and the combined organic extracts were washed with brine (200 mL), dried over sodium sulfate, filtered and spin evaporated in vacuo to a foam. This material was dissolved in ethyl acetate and chromatographed on Silica Gel 60 (E. M. Science, 230–440 mesh) (8 g; 2×7 cm column bed) using ethyl acetate as eluent. The first 100 mL of eluent was collected and spin evaporated in vacuo to give 2.30 g (69% yield) of 2-amino-5-(4-chlorophenoxy)-4-(trans-4-hydroxycyclohexylamino) pyrimidine as a white powder, mp 154–155° C.

Example 4
Preparation of 2-amino-5-(4-chlorophenoxy)-4-(trans-4-hydroxycyclohexylamino)pyrimidine hydrochloride Chromatographically pure 2-amino-5-(4-chlorophenoxy)-4-(trans-4-hydroxycyclohexylamino)pyrimidine (0.93 g, 2.78 mmoles) was dissolved in ethanol (10 mL), concentrated hydrochloric acid (1 mL) was added, and the solution was spin evaporated in vacuo to give a solid. The solid was triturated under ethyl acetate to give a white solid which was collected, washed with ethyl acetate and dried in vacuo to give 0.93 g (90% yield) of 2-amino-5-(4-chlorophenoxy)-4-(trans-4-hydroxycyclohexylamino)pyrimidine hydrochloride as white crystals, mp 155–156° C.

Example 5
Preparation of 2-amino-5-(2,4-dichlorophenoxy)-4-(trans-4-hydroxycyclohexylamino)pyrimidine hydrochloride A solution of oxalyl chloride (Aldrich) (3.91 g, 30.19 mmoles) in dichloromethane (5 mL) was added in several portions to a stirred, ice-bath cooled solution of diisopropylformamide (Aldrich) (4.09 g, 31.02 mmoles) in dichloromethane (100 mL). The ice-bath was removed, and the clear solution was stirred at ambient temperature for 15 minutes. Solid 5-(2,4-dichlorophenoxy)-isocytosine (2,24 g, 8.23 mmoles) was added, and the mixture was refluxed with stirring for 0.5 hour. The resultant solution was cooled and poured into a cold solution of vigorous stirred, saturated aqueous sodium bicarbonate (150 mL). The layers were separated, and the organic phase was washed with cold saturated aqueous sodium bicarbonate (100 mL), with cold water (100 mL) and then dried over sodium sulfate. The dry solution was spin evaporated in vacuo to give the intermediate 4-chloro-5-(2,4-dichlorophenoxy)-2-(diisopropylaminomethyleneamino)pyrimidine as a syrup. The syrup was dissolved in ethanol (100 mL) and trans-4-hydroxycyclohexylamine hydrochloride (Aldrich) (4.97 g, 31.79 mmoles) was added. A solution of sodium ethoxide, which has been prepared from sodium hydride (60% in mineral oil) (Aldrich) (1.19 g, 29.75 mmoles) and ethanol (25 mL) was added, and the reaction was refluxed with stirring for 66 hours. Concentrated hydrochloric acid (21 mL) was added to the cooled reaction mixture, and the reaction was refluxed with stirring for 4 hours. The volatiles were removed by spin evaporation in vacuo. The residue was dissolved in water (200 mL) and extracted with dichloromethane (3×80 mL). The pH of the aqueous solution was adjusted to 8 with 2 M sodium hydroxide. The gummy residue that precipitated was dissolved in dichloromethane (100 mL). The aqueous phase was extracted with dichloromethane (100 mL), and the combined organic extracts were washed with water (5×80 mL), dried over sodium sulfate and spin evaporated in vacuo to a foam. This material was dissolved in ethyl acetate and chromatographed on Silica Gel 60 (E. M. Science, 230–440 mesh) (12×4 cm column bed) using ethyl acetate as the eluent for the first 750 mL and then with 5% ethanol in ethyl acetate. The fractions that contained homogeneous product were spin evaporated in vacuo to give a syrup. The pure 2-amino-5-(2,4-dichlorophenoxy)-4-(trans-4-hydroxycyclohexylamino) pyrimidine was converted to the hydrochloride by the same procedure described in Example 4. Repeated spin evaporation of the residue under ethanol, than ethyl acetate and finally hexanes gave 1.42 g (42% yield) of 2-amino-5-(2,4-dichlorophenoxy)-4-(trans-4-hydroxycyclohexylamino) pyrimidine hydrochloride as a fluffy solid, mp 138–145° C.

Example 6
Preparation of ethyl 4-ethylphenoxyacetate

A mixture of 4-ethylphenol (Aldrich) (14.34 g, 116.20 mmoles), anhydrous potassium carbonate (Aldrich) (20.47 g, 146.63 mmoles), ethyl bromoacetate (Aldrich) (17.01 g, 99.81 mmoles) and dry acetone (Aldrich) (200 mL) was refluxed with stirring under a drying tube for 18 hours. The reaction was cooled, and the volatiles were removed by spin evaporation in vacuo. The white residue was partitioned between ice-cold water (250 mL) and dichloromethane (250 mL). The dichloromethane phase was separated and washed with ice cold water (2×100 mL), an ice-cold solution of 5% aqueous sodium hydroxide (150 mL) and finally with ice-cold water (2×100 mL). The dichloromethane solution was dried over sodium sulfate and spin evaporated in vacuo to give 19.86 g (95% yield) of ethyl 4-ethylphenoxyacetate as a clear liquid, which was one spot on thin layer chromatography.

Example 7
Preparation of 5-(4-ethylphenoxy)-2-(mercapto)pyrimidine-4(3H)-one

A solution of ethyl 4-ethylphenoxyacetate (19.85 g, 95.31 mmoles) and ethyl formate (Acros) (35 mL, 433.25 mmoles) in tetrahydrofuran (100 mL) was added dropwise to a stirred dispersion of sodium hydride (60% dispersion in mineral oil) (Aldrich) (5.53 g, 138.25 mmoles) in tetrahydrofuran (50 mL). After 30 minutes, when about 60% of the solution had been added, the reaction was cooled with an ice-bath to slow the reaction. After a total of 1 hour addition was complete, the addition funnel was rinsed with tetrahydrofuran (15 mL), and the reaction mixture was stirred at ambient temperature for 20 hours. The solution was cooled on an ice-bath. The volatiles were removed by spin evaporation in vacuo to give the sodium salt of ethyl 2-formyl-2-(4-ethylphenoxy)acetate as a brown semisolid. The semisolid was largely dissolved in ethanol (200 mL) and combined with thiourea (Aldrich) (8.79 g, 114.32 mmoles). The reaction mixture was refluxed with stirring for 22 hours and then cooled on an ice-bath. The volatiles were removed by spin evaporation in vacuo to give a semi-solid residue, which was dissolved in water to a volume of 500 mL in a 1.5 L beaker. The solution was covered with hexanes (200 mL) and vigorously stirred. The hexanes layer was decanted and discarded. The hexanes wash procedure was repeated three times. Some insoluble material was removed from the aqueous solution by filtration through flutted filter paper. The filtrate was cooled and acidified by the rapid, dropwise addition of a dilute hydrochloric acid solution (prepared from concentrated hydrochloric acid (12 mL) and water (50 mL)) to the stirred filtrate. Additional water (300 mL) was added during acidification to facilitate stirring. The cream colored solid was collected, washed extensively with water (1800 mL), and vacuum suction air dried to give the crude product. The solid was heated with stirring in hexanes to a final volume of 400 mL. The cooled mixture was collected, washed with hexanes and dried to give 13.00 g (52% yield) 5-(4-ethylphenoxy)-2-(mercapto)pyrimidine-4(3H)-one as a white solid, mp >220° C. Recrystallization of a sample from hexanes-ethyl acetate gave analytically pure 5-(4-ethylphenoxy)-2-(mercapto)pyrimidine-4(3H)-one as a white powder, mp 242–244° C.

Example 8
Preparation of 5-(4-ethylphenoxy)pyrimidine-4(3H)-one

A mixture of 5-(4-ethylphenoxy)-2-(mercapto) pyrimidine-4(3H)-one (2.49 g, 10.28 mmoles), ethanol (250 mL) and wet Raney Ni (50% slurry in water, active catalyst) (Aldrich) (10.9 g) was refluxed with stirring for 3 hours. The reaction was cooled to about 40° C. and filtered through a pad of CELITE 545 (Fisher). The pad was washed with hot ethanol (2×75 mL) and placed in a beaker of water. The combined filtrates were spin evaporated in vacuo to a syrup. The syrup was dissolved in ethyl acetate and reevaporated to give a gray solid. The solid was dissolved in ethyl acetate (40 mL) and applied to a column (4.2×9.5 cm) of Silica Gel 60 (E. M. Science, 230–440 mesh) that was equilibrated with ethyl acetate. The column was eluted with ethyl acetate by flash chromatography, and twelve 100 mL fractions were collected. Fractions 4–10 were combined and spin evaporated in vacuo. The residual oil was dissolved in ethyl acetate and evaporated to give a mixture of light green and white crystals. The crystals were dissolved in dichloromethane and spin evaporated in vacuo to give 1.37 g (63% yield) of 5-(4-ethylphenoxy)pyrimidine-4(3H)-one. Recrystallization of a sample from ethyl acetate gave analytically pure 5-(4-ethylphenoxy)pyrimidine-4(3H)-one as white needles, mp 144–146° C.

Example 9
Preparation of 5-(4-ethylphenoxy)-4-(trans-4-hydroxycyclohexylamino)pyrimidine hydrochloride A solution of oxalyl chloride (Aldrich) (1.97 g, 15.2 mmoles) in dichloromethane (6 mL) was added in several portions to a stirred, ice-bath cooled solution of diisopropylformamide (Aldrich) (2.00 g, 15.17 mmoles) in dichloromethane (25 mL). The ice-bath was removed, and the solution was stirred at ambient temperature for 10 minutes. Solid 5-(4-ethylphenoxy)pyrimidin-4(3H)-one (1.00 g, 4.62 mmoles) was added, and the mixture was refluxed with stirring for 45 minutes. The solution was cooled and poured into a cold solution of vigorously stirred, saturated aqueous sodium bicarbonate (80 mL). The organic layer was washed with cold saturated aqueous sodium bicarbonate (80 mL), with cold water (80 mL) and then dried over sodium sulfate. The dry solution was spin evaporated in vacuo to give the intermediate 4-chloro-5-(4-ethylphenoxy)pyrimidine as an orange liquid. The liquid was dissolved in ethanol (50 mL) and trans-4-hydroxycyclohexylamine hydrochloride (Aldrich) (1.79 g, 11.45 mmoles) was added. A solution of sodium ethoxide, which had been prepared from sodium hydride (60% in mineral oil) (Aldrich) (0.41 g, 10.25 mmoles) and ethanol (15 mL) was added. The flask was rinsed with ethanol (10 mL), and the reaction was refluxed with stirring for 65 hours. The volatiles were removed by spin evaporate in vacuo to a small volume, and the residue was triturated with water (100 mL). The gummy residue was extracted with dichloromethane (150 mL). The solution was washed with water (80 mL), dried over sodium sulfate and spin evaporated in vacuo. This material was dissolved in ethyl acetate-hexanes and chromatographed on Silica Gel 60 (E. M. Science, 230–440 mesh) (13×4 cm column bed) using ethyl acetate as the eluent for the first 1.2 L and then with 5% ethanol in ethyl acetate. The fractions that contained homogeneous product were spin evaporated in vacuo to give a syrup. The pure 5-(4-ethylphenoxy)-4-(trans-4-hydroxycyclohexylamino)pyrimidine was converted to the hydrochloride by the same procedure described in Example 4. The residue was triturated under ethyl acetate to give a white solid which was collected, washed with ethyl acetate and dried in vacuo to give 1.25 g (77% yield) of 5-(4-ethylphenoxy)-4-(trans-4-hydroxycyclohexylamino) pyrimidine hydrochloride as a white solid, mp 245–243° C.

Example 10
Preparation of a 2-amino-5-(4-chlorophenoxy)-4-(4-oxocyclohexylamino)pyrimidine hydrochloride Acetic anhydride (0.61 g, 5.8 mmoles) and pyridine (0.96 g, 11.9 mmoles) were added to an ice-bath cooled suspension of chromium(IV) oxide (Aldrich) (0.61 g, 6.1 mmoles) in dichloromethane (11 mL). The mixture was stirred at ambient temperature for 20 minutes, and 2-amino-5-(4-chlorophenoxy)-4-(trans-4-hydroxycyclohexylamino)

pyrimidine (0.65 g, 1.87 mmoles) was added, followed by dichloromethane (10 mL). The mixture was stirred for 1.25 hours and poured into cold ethyl acetate (200 mL), stirred for 15 minutes and filtered through a pad of CELITE 545 (Fisher). The filtrate was filtered through flutted filter paper and then spin evaporated in vacuo. The residue was purified by flash column chromatography on Silica Gel 60 (E. M. Science, 230–440 mesh) (2×16 cm) using ethyl acetate as the eluant. The fractions that contained homogeneous product were spin evaporated in vacuo to give a syrup. The flash column chromatography was repeated. The pure 2-amino-5-(4-chlorophenoxy)-4-(4-oxocyclohexylamino)pyrimidine was converted to the hydrochloride by the same procedure described in Example 4. The residue was triturated under ethyl acetate to give a white solid which was collected, washed with ethyl acetate and dried in vacuo to give 0.29 g (41% yield) of 2-amino-5-(4-chlorophenoxy)-4-(4-oxocyclohexylamino)pyrimidine hydrochloride as a white solid. [Method modeled after M. J. Robins et al. J. Med. Chem., 35, 2283–2293 (1992)]

Example 11
Preparation of 2-amino-5-(4-chlorophenoxy)-4-(4-hydroxyanilino)pyrimidine hydrochloride Nitrogen was bubbled through a suspension of 10.11 g (27.5 mmol) of 4-chloro-5-(4-chlorophenoxy)-2-(diisopropylaminomethyleneamino)pyrimidine (see Example 2) in 205 ml of methanol for 10 minutes. Then 3.18 g (29.1 mmol) of 4-aminophenol was added and nitrogen bubbled through the suspension for 5 minutes. The solution was then tightly sealed and stirred at 24° C. for 20 hours. Then 50 ml of concentrated hydrochloric acid was added to the mixture and refluxed for 140 minutes. The mixture was cooled and spin evaporated to one-half the original volume and then stored at 3° C. After 3 hours, a large precipitate had formed which was collected by filtration and washed quickly with cold methanol. The filter cake was suspended in 79 ml of $CH_2Cl_2$ and the suspension was boiled for 5 minutes. The solids were collected by filtration, washed with $CH_2Cl_2$ and dried in vacuo at 100° C. 8.6 g (86%) of product as a pale yellow powder was obtained, mp 288–289° C.

Example 12
Preparation of 2-amino-5-(4-chlorophenoxy)-4-(4-hydroxy-2-methylanilino)pyrimidine Nitrogen was bubbled through a suspension of 2 g (9 mmol) of 4-chloro-5-(4-chlorophenoxy)-2-(diisopropylaminomethyleneamino)pyrimidine (see Example 2) in 20 ml of ethanol for 10 minutes. Then 1.15 g (9.34 mmol) of 4-amino-3-methylphenol was added and nitrogen bubbled through the suspension for 5 minutes. The solution was then tightly sealed and stirred at 24° C. for 20 hours. Then 5 ml of concentrated hydrochloric acid was added to the mixture and refluxed for 60 minutes. The mixture was cooled and spin evaporated. The residue was suspended in 100 mL $CH_2Cl_2$ and 400 mL water. The pH was adjusted to 12 with 3N NaOH. The organic phase was washed with water (400 mL) twice, brine (200 mL) and then dried over $Na_2SO_4$. The salt was removed by filtration and the filtrate applied to a Silica Gel 60 column (2.5×10 cm) preequilibrated with $CH_2Cl_2$. The column was eluted with 800 mL $CH_2Cl_2$ and then with mixtures of ethylacetate and $CH_2Cl_2$. The fractions showing one spot on TLC (EtOAc; Rf0.45) were pooled and concentrated by spin evaporation. The liquor formed crystals on standing. 0.19 g (6% yield) of product, a white solid, was obtained after drying in vacuo at 105° C. for 16 hours, mp 199–201° C.

Example 13

Preparation of 4-(4-acetoxyanilino)-2-amino-5-(4-chlorophenoxy)pyrimidine 1.26 g (3.45 mmoles) of 2-amino-5-(4-chlorophenoxy)-4-(4-hydroxyanilino)pyrimidine hydrochloride (see Example 11) and 0.05 g of 4-dimethylaminopyridine were dissolved in 3.2 g of dry N,N-dimethylformamide. 5.3 g of acetic anhydride was added, and the container was sealed. After 5 days at 24° C., 100 mL of $CH_2Cl_2$ were added to the reaction mixture and stirred with 150 mL of cold saturated aqueous $NaHCO_3$. The organic layer was then washed twice with 250 mL of water, then with 200 mL of brine and dried over $Na_2SO_4$. After filtering off the salt, the filtrate was applied to a Silica Gel 60 column (2.5×7.5 cm) which had been preequalibrated with hexanes. The column was eluted with 200 mL hexanes, a mixture of 100 mL hexanes and 200 mL $CH_2Cl_2$, and 500 mL $CH_2Cl_2$. Fractions with product which was pure by TLC (EtOAc; Rf 0.6) were pooled and spin evaporated to a waxy solid. This solid was removed from the flask with the aid of hot hexanes. After cooling, solids were collected by filtration and washed with hexanes. After drying in vacuo at 89° C. for 16 hours, the product, a cream colored powder, 0.14 g (11% yield), was obtained, mp 132–133° C.

The following additional compounds of the present invention were prepared by methods analogous to those described above:

| Chemical Name | MP° C. |
|---|---|
| 2-Amino-5-(4-chlorophenoxy)-4-(trans-4-hydroxycyclohexylamino)pyrimidine.HCl | 155–156 |
| 2-Amino-5-(4-chlorophenoxy)-4-(trans-2-hydroxycyclohexylamino)pyrimidine.HCl | 175–180 |
| 2-Amino-5-(4-chlorophenoxy)-4-(cyclohexylamino)pyrimidine | 90–95 |
| 2-Amino-5-(4-chlorophenoxy)-4-(2-hydroxyethylamino)-pyrimidine | 154–155 |
| 2-Amino-5-(4-chlorophenoxy)-(4-hydroxypentylamino)-pyrimidine | 160–161 |
| 2-Amino-5-(4-chlorophenoxy)-4-(2-hydroxy-1-methyl(ethylamino))pyrimidine | 193–194 |
| 2-Amino-5-(4-chlorophenoxy)-4-(1,1-dimethyl-2-hydroxyethylamino)pyrimidine | 142–143 |
| 2-Amino-5-(4-chlorophenoxy)-4-(2-hydroxypropylamino)-pyrimidine.HCl | 138–140 |
| 2-Amino-5-(4-chlorophenoxy)-4-(1-ethyl-2-hydroxyethylamino)pyrimidine.HCl | 88–90 |
| 2-Amino-5-(4-chlorophenoxy)-4-bis(2-hydroxyethyl)amino)pyrimidine | 148–150 |
| 2-Amino-5-(4-ethylphenoxy)-4-(trans-4-hydroxycyclohexylamino)pyrimidine.HCl | 245–253 |
| 2-Amino-5-(4-chlorobenzyl)-4-(trans-4-hydroxycyclohexylamino)pyrimidine | 85–87 |
| 2-Amino-5-(4-chlorophenoxy)-4-(2-(2-proprionyloxyethoxy)ethylamino)pyrimidine hydrochloride | 99–100 |
| 2-Amino-5-(4-chlorophenoxy)-4-(4-hydroxy-2-chloroanilino)pyrimidine | 225 |
| 2-Amino-5-(4-chlorophenoxy)-4-(4-hydroxy-3-chloroanilino)pyrimidine | 221 |

The following examples illustrate representative pharmaceutical compositions where the "Active Ingredient" may be any compound of Formula (I) or a pharmaceutically acceptable salt thereof.

Example A—Tablet Composition

|  | mg/tablet |
|---|---|
| (a) Active Ingredient | 250 |
| (b) Lactose B.P. | 210 |
| (c) Povidone B.P. | 15 |
| (d) Sodium Starch Glycollate | 20 |
| (e) Magnesium Stearate | 5 |

The composition is prepared by wet granulation of the ingredients with a solution of povidone, followed by addition of magnesium stearate and compression.

Example B—Capsule Composition

A capsule composition is prepared by admixing the ingredients and filling into a two-part hard gelatin capsule.

|  | mg/capsule |
|---|---|
| (a) Active Ingredient | 250 |
| (b) Lactose B.P. | 143 |
| (c) Sodium Starch Glycollate | 25 |
| (d) Magnesium Stearate | 2 |

Example C—Injectable Composition

| (a) | Active Ingredient | 0.200 g |
|---|---|---|
| (b) | Hydrochloric Acid Solution 0.1 M or Sodium Hydroxide Solution 0.1 M to a pH of: | 4.0 to 7.0 |
| (c) | Sterile Water q.s. to: | 10 ml |

The active ingredient is dissolved in most of the water (35°–40° C.) and the pH is adjusted to between 4.0 and 7.0. The batch is then made up to volume with sterile water and filtered through a sterile micropore filter into a sterile amber glass vial (type 1) and sealed with sterile closures and overseals.

The compounds of the present invention were assayed for neurotrophic activity as follows:

A. Screen for NGF-like Activity:

Cultured PC12 cells (rat adrenal pheochromocytoma from ATCC) have receptors for NGF. Responses include promotion of neurite outgrowth and elevation of choline acetyltransferase (ChAT) (L. A. Green and A. S. Tischler, Cell Neurobiol., 3, 373 (1982)).

The following assay is modified from that described in H L White and P W Scates, Neurochem. Res., 16, 63 (1991). PC12 cells were cultured at 37° C. in RPMI supplemented with HEPES buffer, pH 7.5 (to 10 mM), fetal bovine serum, horse serum, glutamine, penicillin, streptomycin and nonessential amino acids. Cultures were split 1:3 every 3 to 4 days. Exponentially dividing cells were plated into fresh medium on collagen-coated 12-well plastic dishes ($10^5$ cells/well). After allowing one day for cell attachment, the medium was replaced with low serum medium, with or without test compounds with each condition in triplicate. The medium may contain up to 0.2% ethanol, which was used as a solvent for most compounds tested. Cells were examined for morphological changes using an Olympus IMT-2 inverted research microscope. After 3 days incubation with test compounds, medium was removed and replaced with 0.2 ml of lysis and ChAT assay mixture. The plates were incubated at 37° C. for 2 hours and then placed into a freezer at −20° C.

Compounds are judged NGF-like in this primary screen if they (1) increase the activity of ChAT, (2) enhance NGF-stimulated neurite outgrowth or (3) potentiate or appear additive with the action of NGF itself.

B. Choline Acetyltransferase (ChAT) Assays:

The assay mixture contained 100 mM phosphate, pH 7.4, 0.1% NP-40, 150 mM NaCl, 1.5 mM choline, 10 mM EDTA, 0.1 mM eserine, 0.1 mM acetyl-coenzyme A and about 0.5 uCi (40–70 Ci/mol) [14C]acetyl-coenzyme A in each ml of mixture. Thawed and lysed cell reaction mixtures were diluted to 1 ml with water and transferred to 7 ml scintillation vials containing 5 ml of extraction/scintillation fluid solution (50 mg triphenyl borate, 50 mg PPO, 20 mg POPOP per 100 ml of 20% acetonitrile/80% toluene) and vortexed for 10 seconds. After all diluted well contents were transferred and mixed, all the vials were vortexed again for 30 seconds, rotated for about 2 hours, and then vortexed once more. The vials were centrifuged at 3000 rpm (max.= 16 cm) for 15 minutes and then counted in a Beckman LS6500 scintillation counter. Background counts from reaction mixtures with extracts from nonstimulated cells (no NGF and no test compound) were subtracted from reaction product counts before comparisons of ChAT activities were made.

The following data were obtained for representative compounds of the present invention which (1) increased the activity of choline acetyltransferase ChAT), (2) enhanced NGF-stimulated neurite outgrowth and/or (3) potentiated or appeared additive with the action of NGF itself. The concentration at which the test compound doubled the ChAT activity over the activity with NGF alone (no test compound) was recorded as the $EC_{2x}$ value:

| Compound of | $EC_{2x}$ (uM) |
|---|---|
| Example 3 | 0.4 |
| Example 5 | 1.2 |
| Example 10 | 0.7 |

What is claimed is:

1. A compound of the formula

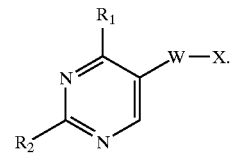

wherein

W is O, $CH_2$, $CH_2CH_2$, $OCH_2$ or $CH_2CH_2CH_2$; $R_1$ is $NR_4R_5$ wherein $R_4$ and $R_5$ are independently H, OH, C6-10aryl, C2-6alkoxy, C6-10aryloxy, or (C1-6alkyl)j(C6-10aryl)($CH_2$)q (wherein J is 0 or 1 and q is 0–6), provided that when $R_4$ is H or OH, then $R_5$ is not H or OH, and wherein the C atoms of $R_4$ and $R_5$ may optionally be substituted with one or more substituents selected from the group consisting of:

OH;

halogen;

thio;

thio-oxo;

oxo;
C1-6alkyl;
C2-7alkenyl;
C2-7alkynyl;
C6-10aryl;
C6-10heteroaryl;
hydroxyC1-6alkyl;
dihydroxyC1-6alkyl;
C1-6alkoxy;
C1-6aryloxy;
C6-10heteroaryloxy;
hydroxyC1-6alkoxy;
C1-6alkoxyC1-6alkyl;
C6-10aryloxyC1-6alkyl;
C6-10heteroaryloxyC1-6alkyl;
C3-8cycloalkyl;
C6-10arylC1-6alkyl;
C6-10arylC1-6alkoxy;
C6-10heteroarylC1-6alkoxy;
C1-6alkylcarbonylC1-6alkyl;
C6-10arylcarbonylC1-6alkyl;
carboxyC1-6alkyl;
C1-6alkoxycarbonylC1-6alkyl;
C6-10aryloxycarbonylC1-6alkyl;
C6-10arylC1-6alkyloxycarbonylC1-6alkyl;
cyanoC1-6alkyl;
C1-6alkylthioC1-6alkyl;
C1-6alkylsulfinylC1-6alkyl;
C1-6alkylsulfonylC1-6alkyl;
C6-10arylthioC1-6alkyl;
C6-10arylsulfinylC1-6alkyl;
C6-10arylsulfonylC1-6alkyl;
C6-10arylC1-6alkylthioC1-6alkyl;
C6-10arylC1-6alkylsulfinylC1-6alkyl;
C6-10arylC1-6alkylfulfonylC1-6alkyl;
C6-10heteroarylthioC1-6alkyl;
C6-10heteroarylsulfinylC1-6alkyl;
C6-10heteroarylsulfonylC1-6alkyl;
aziridino;
azetidino;
pyrrolidino;
piperidino;
heptamethyleneimino;
homopiperazino;
N-substituted homopiperazino (wherein the substituent may be C1-6alkyl, C6-10aryl, C6-10arylC1-6alkyl or C6-10heteroaryl);
piperazino;
N-substituted piperazino (wherein the substituent may be C1-6alkyl, C6-10aryl, C6-10arylC1-6alkyl or C6-10heteroaryl);
morpholino;
homomprpholino;
thiomorpholino;
aminoC1-6alkyl;
C1-6alkylaminoC1-6alkyl;
di(C1-6alkyl)aminoC1-6alkyl (wherein the alkyl groups may be the same or different);
C6-10arylaminoC1-6alkyl;
C6-10arylC1-6alkylaminoC1-6alkyl;
di(C6-10aryl)aminoC1-6alkyl (wherein the aryl groups may be the same or different);
di(C6-10arylC1-6alkyl)aminoC1-6alkyl (wherein the arylalkyl groups may be the same or different);
$R_{12}$C(O)C1-6alkyl (wherein $R_{12}$ is aziridino, azetidino, pyrrolidino, piperidino, heptamethyleneimino, piperazino, homopiperazino, morpholino, homomorpholine, or thiomorpholino);
C(O)$R_6$; C(O)C(O)$R_6$; C(S)$R_6$; S(O)$_2$$R_6$; and C(N$R_{11}$)$R_6$ (wherein $R_{11}$ is H, C1-6alkyl or C6-10aryl and $R_6$ is H, C1-6alkyl, C1-6alkyl, C6-10aryl, C6-10arylC1-6alkyl or C6-10heteroaryl);

$R_2$ is H or $NH_2$, provided that when W is $CH_2$, then $R_2$ is $NH_2$;

X is a C6-10 aryl ring or a C6-10 heteroaryl ring optionally substituted with one or more substituents Y selected from the group consisting of:
halogen;
C1-6 alkyl;
C2-7alkenyl;
C2-7alkynyl;
C6-10aryl;
C6-10heteroaryl;
OR (wherein R is H, C1-6alkyl, C3-8cycloalkyl, C6-10aryl or C6-10arylC1-6alkyl);
N$R_9$$R_{10}$ (wherein $R_9$ and $R_{10}$ may be the same or different and are H, C1-6alkyl, C3-8cycloalkyl, C6-10aryl, or C6-10arylC1-6alkyl);
NROR;
C(O)N$R_9$$R_{10}$;
C(O)OR;
C(O)R;
NRC(O)N$R_9$$R_{10}$;
NRC(O)R;
NRC(O)OR;
CR(OH)R;
OC(O)R;
S(O)nR' (wherein R' is C1-6alkyl, C3-8cycloalkyl, C6-10aryl or C6-10arylC1-6alkyl and n is 0, 1 or 2);
NRS(O)mR' (wherein m is 1 or 2);
S(O)$_2$N$R_9$$R_{10}$;
$NO_2$;
CN;
$CF_3$; and
$OCF_3$;
wherein each C6-10heteroaryl group is an aryl ring having 1 to 4 carbon atoms replaced by heteroatoms selected from the group consisting of N, O and S; or a pharmaceutically acceptable ester, amide or salt thereof.

2. A compound according to claim 1, wherein W is O or $CH_2$ and X is substituted phenyl.

3. A compound according to claim 1, wherein $R_1$ is 4-hydroxyanilino or 4-hydroxybenzylamino; W is O; X is phenyl optionally substituted with 4-chloro, 2,4-dichloro, 4-bromo, 2-fluoro-4-chloro, 2-chloro-4-fluoro, 2-methyl-4-chloro, 4-methyl, or 4-ethyl; and $R_2$ is $NH_2$.

4. A compound of the formula

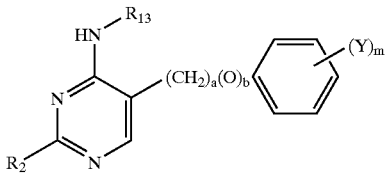

wherein a and b are 0 or 1 and a+b=1; m is 0–2; $R_2$ is H or $NH_2$, provided that when a is 1, then $R_2$ is $NH_2$; $R_{13}$ is phenyl or benzyl optionally substituted with up to three substituents selected from the group consisting of:
OH;
halogen;
C1-6alkyl;
hydroxyC1-6alkyl;
dihydroxyC1-6alkyl;
C1-6alkoxy;
hydroxyC1-6alkoxy;
C1-6alkoxyC1-6alkyl, and
carboxyC1-6alkyl;
and each Y is selected from the group consisting of:
  halogen;
  C1-6 alkyl;
  C2-7alkenyl;
  C2-7alkynyl;
  C6-10aryl;
  C6-10heteroaryl;
  OR (wherein R is H, C1-6alkyl, C3-8cycloalkyl, C6-10aryl or C6-10arylC1-6alkyl);
  $NR_9R_{10}$ (wherein $R_9$ and $R_{10}$ may be the same or different and are H, C1-6alkyl, C3-8cycloalkyl, C6-10aryl, or C6-10arylC1-6alkyl);
  NROR;
  $C(O)NR_9R_{10}$;
  C(O)OR;
  C(O)R;
  $NRC(O)NR_9R_{10}$
  NRC(O)R;
  NRC(O)OR;
  CR(OH)R;
  OC(O)R;
  S(O)nR' (wherein R' is C1-6alkyl, C3-8cycloalkyl, C6-10aryl or C6-10arylC1-6alkyl and n is 0, 1 or 2);
  NRS(O)mR' (wherein m is 1 or 2);
  $S(O)_2NR_9R_{10}$;
  $NO_2$;
  CN;
  $CF_3$; and
  $OCF_3$;
wherein each C6-10heteroaryl group is an aryl ring having 1 to 4 carbon atoms replaced by heteroatoms selected from the group consisting of N, O and S; or a pharmaceutically acceptable ester, amide or salt thereof.

5. A compound according to claim 4, wherein $R_{13}$ is phenyl substituted with 1 or 2 hydroxyl groups.

6. A compound according to claim 4, wherein $R_{13}$ is benzyl substituted with 1 or 2 hydroxyl groups.

7. A compound selected from the group consisting of:
2-Amino-4-(4-hydroxyanilino)-5-(4-chlorophenoxy) pyrimidine;
2-Amino-4-(4-hydroxyanilino)-5-(2,4-dichlorophenoxy) pyrimidine;
2-Amino-4-(4-hydroxyanilino)-5-(4-bromophenoxy) pyrimidine;
2-Amino-4-(4-hydroxyanilino)-5-(2-fluoro-4-(chlorophenoxy)pyrimidine;
2-Amino-4-(4-hydroxyanilino)-5-(2-chloro-4-(fluorophenoxy)pyrimidine;
2-Amino-4-(4-hydroxyanilino)-5-(2-methyl-4-(chlorophenoxy)pyrimidine;
2-Amino-4-(4-hydroxyanilino)-5-(4-methylphenoxy) pyrimidine;
2-Amino-4-(4-hydroxyanilino)-5-(4-ethylphenoxy) pyrimidine;
2-Amino-5-(4-chlorophenoxy)-4-(4-hydroxy-2-methylanilino)pyrimidine;
2-Amino-5-(4-chlorophenoxy)-4-(2-hydroxy-4-methylanilino)pyrimidine;
4-(4-Acetoxyanilino)-2-amino-5-(4-chlorophenoxy) pyrimidine;
2-Amino-5-(4-chlorophenoxy)-4-(2-(2-proprionyloxyethoxy)ethylamino) pyrimidine hydrochloride;
2-Amino-5-(4-chlorophenoxy)-4-(4-hydroxy-2-chloroanilino)pyrimidine;
2-Amino-5-(4-chlorophenoxy)-4-(4-hydroxy-3-chloroanilino)pyrimidine;
2-Amino-4-(methoxyamino)-5-(4-chlorophenyloxy) pyrimidine;
2-Amino-4-(2-hydroxyethoxyamino)-5-(4-chlorophenoxy)pyrimidine;
2-Amino-4-(4-hydroxyanilino)-5-phenoxypyrimidine;
2-Amino-4-(4-hydroxy-2-methylanilino)-5-phenoxypyrimidine;
2-Amino-4-(4-hydroxyanilino)-5-(2-chlorophenoxy) pyrimidine;
2-Amino-4-(4-hydorxy-2-methylanilino)-5-(2-chlorophenoxy)pyrimidine;
2-Amino-4-(4-hydroxyanilino)-5-(4-chloro-2-methylphenoxy)pyrimidine;
2-Amino-4-(4-hydroxy-2-methylanilino)-5-(4-chloro-2-methylphenoxy)pyrimidine;
2-Amino-4-(4-hydroxyanilino)-5-(4-chloro-2-methylphenoxy)pyrimidine;
2-Amino-4-(4-hydroxyanilino)-5-(4-butylphenoxy) pyrimidine;
2-Amino-4-(4-hydroxy-2-methylanilino)-5-(4-butylphenoxy)piperidine;
2-Amino-4-(4-hydroxyanilino)-5-(4-methoxyphenoxy) pyrimidine;
2-Amino-4-(4-hydroxy-2-methylanilino)-5-(4-methoxyphenoxy)pyrimidine; and
2-Amino-4-(4-hydroxy-2-methylanilino)-5-(2-methoxyphenoxy)pyrimidine.

8. A pharmaceutical composition, comprising a compound according to claim 1 and a pharmaceutically acceptable carrier therefor.

9. A pharmaceutical composition, comprising a compound according to claim 4 and a pharmaceutically acceptable carrier therefor.

10. A pharmaceutical composition, comprising a compound according to claim 7 and a pharmaceutically acceptable carrier therefor.

11. A method of treating a mammal having a neurodegerative or neurological disorder of the central or peripheral nervous system, which comprises administering to said mammal a therapeutically effective amount of a compound according to claim 1.

12. A method according to claim 11, wherein the disorder is a dementing disorder.

13. A method according to claim 12, wherein the disorder is Alzheimer's disease.

14. A method according to claim 12, wherein the disorder is senile dementia.

15. A method according to claim 11, wherein the disorder is peripheral neuropathy.

16. A method according to claim 11, wherein the disorder is a nerve injury.

17. A method of treating a mammal having a neurodegenerative or neurological disorder of the central or peripheral nervous system, which comprises administering to said mammal a therapeutically effective amount of a compound according to claim 4.

18. A method according to claim 17, wherein the disorder is a dementing disorder.

19. A method according to claim 18, wherein the disorder is Alzheimer's disease.

20. A method according to claim 18, wherein the disorder is senile dementia.

21. A method according to claim 17, wherein the disorder is peripheral neuropathy.

22. A method according to claim 17, wherein the disorder is a nerve injury.

23. A method of treating a mammal having a neurodegenerative or neurological disorder of the central or peripheral nervous system, which comprises administering to said mammal a therapeutically effective amount of a compound according to claim 7.

24. A method according to claim 23, wherein the disorder is a dementing disorder.

25. A method according to claim 24, wherein the disorder is Alzheimer's disease.

26. A method according to claim 24, wherein the disorder is senile dementia.

27. A method according to claim 23, wherein the disorder is peripheral neuropathy.

28. A method according to claim 23, wherein the disorder is a nerve injury.

* * * * *

UNITED STATES PATENT AND TRADEMARK OFFICE
CERTIFICATE OF CORRECTION

PATENT NO.    : 6,916,820 B1
DATED         : July 12, 2005
INVENTOR(S)   : Kelley et al.

It is certified that error appears in the above-identified patent and that said Letters Patent is hereby corrected as shown below:

Column 4,
Line 50, "C8-10 aryl" should read -- C6-10 aryl --.
Line 61, "NR8R10 (wherein R8" should read -- NR9R10 (wherein R9 --.
Line 63, "C8-10arylC1-6alkyl" should read -- C6-10arylC1-6alkyl --.

Column 5,
Lines 52-60, "Formula 1A should read:

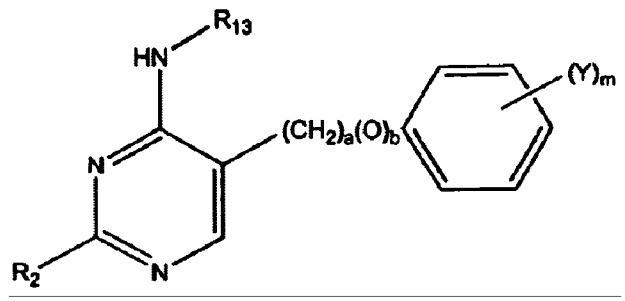

Line 61, "a+b-1" should read -- a+b=1 --.

Column 25,
Line 61, "homomprpholino" should read -- homomorpholino --.

Column 26,
Line 11, "homomorpholine" should read -- homomorpholino --.

Column 28,
Line 38, "(4-hydorxy-2-methylanilino)" should read -- (4-hydroxy-2-methylanilino) --.
Lines 44-45, please cancel compound "2-Amino-4-(4-hydroxyanilino)-5-(4-chloro-2-methylphenoxy)pyrimidine".

UNITED STATES PATENT AND TRADEMARK OFFICE
CERTIFICATE OF CORRECTION

PATENT NO.   : 6,916,820 B1
DATED        : July 12, 2005
INVENTOR(S)  : Kelley et al.

It is certified that error appears in the above-identified patent and that said Letters Patent is hereby corrected as shown below:

Column 28 (cont'd),
Line 49, "piperidine" should read -- pyrimidine --.

Signed and Sealed this

Twenty-fifth Day of October, 2005

JON W. DUDAS
*Director of the United States Patent and Trademark Office*